United States Patent
Joksch et al.

(10) Patent No.: US 10,892,033 B2
(45) Date of Patent: Jan. 12, 2021

(54) METHOD FOR MONITORING BIOPROCESSES

(71) Applicant: Siemens Aktiengesellschaft, Munich (DE)

(72) Inventors: Martin Joksch, St. Andrae-Woerdern (AT); Johannes Scheiblauer, Neuhofen/Ybbs (AT)

(73) Assignee: Siemens Aktiengesellschaft, Munich (DE)

( * ) Notice: Subject to any disclaimer, the term of this patent is extended or adjusted under 35 U.S.C. 154(b) by 519 days.

(21) Appl. No.: 15/704,336

(22) Filed: Sep. 14, 2017

(65) Prior Publication Data
US 2018/0082011 A1    Mar. 22, 2018

(30) Foreign Application Priority Data
Sep. 16, 2016  (EP) ................................ 16189105

(51) Int. Cl.
| | | |
|---|---|---|
| *G01N 33/48* | (2006.01) | |
| *G01N 33/50* | (2006.01) | |
| *G16B 5/00* | (2019.01) | |
| *C12M 1/34* | (2006.01) | |

(Continued)

(52) U.S. Cl.
CPC ............ *G16B 5/00* (2019.02); *C12M 41/00* (2013.01); *C12M 41/48* (2013.01); *C12Q 3/00* (2013.01)

(58) Field of Classification Search
None
See application file for complete search history.

(56) References Cited

U.S. PATENT DOCUMENTS

2015/0302318 A1  10/2015  Chen et al.
2016/0208212 A1   7/2016  Delaroche et al.

FOREIGN PATENT DOCUMENTS

| CN | 102231057 | 11/2011 |
|---|---|---|
| CN | 102829967 | 12/2012 |
| CN | 105473702 | 4/2016 |

(Continued)

OTHER PUBLICATIONS

Variance, in M. Clugston, The Pengun Dictionary of Science (4th ed.) London, UK: Penguin. Retrieved from credoreference.com on Dec. 21, 2019. (Year: 2014).*

(Continued)

*Primary Examiner* — Russell S Negin
(74) *Attorney, Agent, or Firm* — Cozen O'Connor

(57) ABSTRACT

A method of monitoring bioprocesses, wherein a course of a bioprocess is predicted using a process model and values for process parameters are estimated during the bioprocess, where at least one process parameter is selected (step a), for which current measured values are determined during the bioprocess, the respective current measured value of the selected process parameter is compared with the corresponding estimated value for this process parameter estimated by the process model (step b), a variance is then compared with a predetermined threshold value (step c), in a step d), at least one model parameter is then changed when the threshold value is exceeded by the variance, where steps b) to d) are executed until the variance fails to meet the threshold value, and in the case that the threshold value is not met after a predetermined number of repetitions, the method is discontinued and a warning is output.

8 Claims, 1 Drawing Sheet

(51) Int. Cl.
*C12M 1/36* (2006.01)
*C12Q 3/00* (2006.01)

(56) References Cited

FOREIGN PATENT DOCUMENTS

| DE | 10141556 | 3/2003 |
|---|---|---|
| DE | 10141557 | 3/2003 |
| DE | 102007047175 | 4/2009 |
| EP | 2530629 | 12/2012 |

OTHER PUBLICATIONS

Sonnleitner, B. and Käppeli, O. (1986); *Growth of S. cerevisiae is controlled by its limited respiratory capacity: Formulation and verification of a hypothesis.* Biotechnology and Bioengineering, vol. 28: pp. 927-937.

Karakuzu, C. et al. (2006); *Modelling, on-line state estimation and fuzzy control of production scale fed-batch baker's yeast fermentation.* Control Engineering Practice, 14: 959-974.

Nagy, Z.K. (2007) *Model based control of a yeast fermentation bioreactor using optimally designed artificial neural networks.* Chemical Engineering Journal 127 (1): 95-109.

Besenhard, M. O. et al. (2016) *Multivariate Process Control of a Small Scale Bioreactor in a PAT Environment.* Journal of Intelligent Manufacturing, pp. 1-14.

Charbonnier et al, "A self-tuning adaptive trend extraction method for process monitoring and diagnosis" *Journal of Process Control,* Elsevier, 2012, 22 (6), pp. 1127-1138.

Huaiping et al., Multi-model adaptive soft sensor modeling method using local learning and online support vector regression for non-linear time-variant batch variant batch processes, Chemical Engineering Science vol. 131, Jul. 28, 2015, pp. 282-303.

European Search Report dated Mar. 10, 2017.

\* cited by examiner

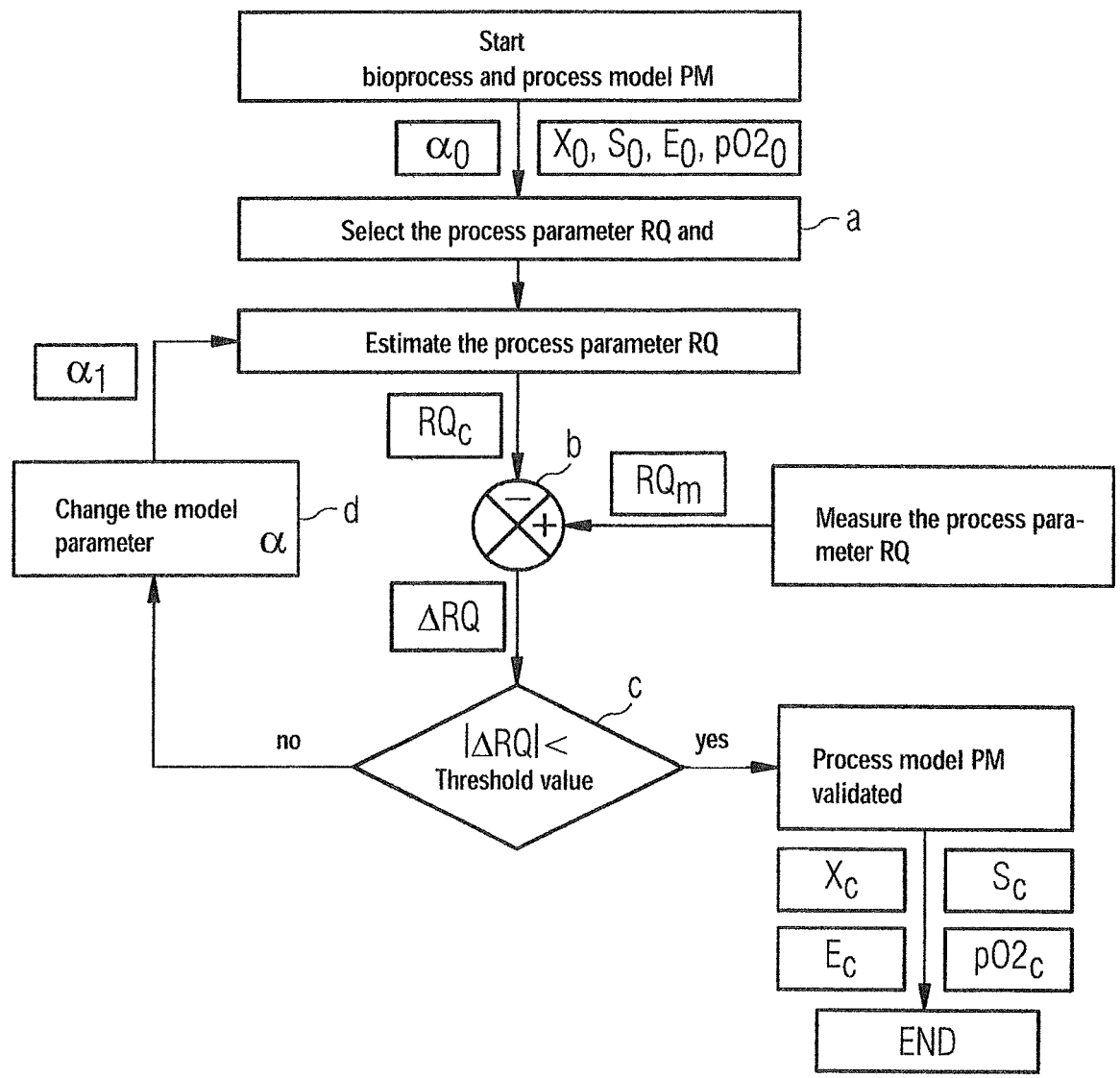

METHOD FOR MONITORING BIOPROCESSES

BACKGROUND OF THE INVENTION

Field of the Invention

The field of the invention generally relates to the field of biotechnology and what is known as bioengineering and, more particularly, to a method of monitoring bioprocesses, in particular fermentation processes, where a course of a bioprocess, in particular a fermentation process, is predicted using a process model and during the course of the bioprocess estimated values for important, biological process parameters are estimated with the aid of the process model.

Description of the Related Art

Bioprocesses, in which living systems, such as cells, organisms, fungi, or bacteria used to produce substances, are employed in various industrial sectors (e.g., food and beverage industry, biopharmaceutical industry, or manufacture of biofuel). In particular, fermentation processes represent a key technology, e.g., in the production of beer, whiskey or wine, in the production of biofuel or in the production of vaccines or antibiotics. Within biotechnology, fermentation is typically understood to mean an enzymatic conversion of organic raw materials (a substrate such as sugar, or glucose) into, e.g., acids, gases or alcohol. Bioprocesses, such as fermentation, are deliberately triggered by adding bacteria, fungi or other biological cell cultures, known as biomass, to a substrate.

Bioprocesses typically occur in what are known as bioreactors, in which the environmental and reaction conditions can be controlled and optimized. For fermentation processes, the bioreactors are also referred to as fermentors. In this way, the desired substance can be produced from the biomass used under conditions that are as optimal as possible, or in a desired concentration. In the bioreactor, various environmental and/or process parameters can be regulated and controlled for the respective bioprocess, such as pH value, temperature, oxygen supply, nitrogen supply, glucose content or mixer settings. However, bioprocesses are biologically complex and very sensitive. Constant close monitoring of the bioprocess is therefore necessary to maintain the corresponding environmental conditions in the bioreactor for a consistent and optimal course of the bioprocess and so that the biomass or the bioactive cells used in the nutrient solution grow and can produce the desired substance.

Mathematical modeling, in which a mathematical process model is developed for the respective bioprocess or fermentation process, represents an important cornerstone in the monitoring of bioprocesses, in particular fermentation processes, for instance. With the aid of this process model, a course of the bioprocess or the fermentation can be predicted, for instance. Furthermore, the process model can be used to mathematically estimate variables of the bioprocess that cannot be measured directly, known as soft sensors, and important process parameters (e.g., a concentration of the biomass, of the glucose, of the substance produced, of the dissolved oxygen etc., a fermenter volume etc.) for each time segment in the entire course of the process.

In the mathematical modeling of bioprocesses, a distinction can typically be made between two groups of modeling approaches, which are known as the deterministic approach and the static approach. With the deterministic approach or with a deterministic process model, known biochemical processes inside and outside of the bioactive cells of the bioprocess are described using mathematical equations, such as differential equations. The publication Sonnleitner, B. and Käppeli, O. (1986); *Growth of S. cerevisiae is controlled by its limited respiratory capacity*: Formulation and verification of a hypothesis. Biotechnology and Bioengineering, Vol. 28: pages 927-937, for instance, discloses a deterministic process model with which fundamental metabolic pathways of the microorganism *Saccharomyces cerevisiae* or *S. cerevisiae* (baker's yeast) are described mathematically.

With the static approach to the mathematical modeling of process models, historical or static data of the respective bioprocess is, in most instances, mathematically processed, where with process models according to the static approach, a deterministic process model is frequently combined with static or stochastic approaches. The rather complex static model approaches only became practicable as computing power increased. The prediction of the respective course of the process or the estimation of process parameters can be carried out for instance using neural networks, such as described in the publications Karakuzu, C. et al. (2006); *Modelling, on-line state estimation and fuzzy control of production scale fed-batch baker's yeast fermentation*. Control Engineering Practice, 14: 959-974. or Nagy, Z. K. (2007); *Model based control of a yeast fermentation bioreactor using optimally designed artificial neural networks*. Chemical Engineering Journal 127 (1): 95-109 or using what is known as the "Golden Batch" Model, such as described e.g. in the publication: Besenhard, M. O. et al. (2016); *Multivariate Process Control of a Small Scale Bioreactor in a PAT Environment*. Journal of Intelligent Manufacturing, pages 1-14.

For monitoring a bioprocess, a prediction produced with the corresponding process model can be compared, for instance, with measurements that are performed during the course of the bioprocess. In the case of variances, intervention by an operator or, with a corresponding regulation, such as by the process model itself, can be initiated. The publication EP 2 350 629 A2 discloses a method of modeling and simulating a fermentation process for brewing beer for instance. In such cases, a concentration of at least one substrate of the fermentation process is determined at a first time instant. For a subsequent, second time instant, the concentration of the at least one substrate of the fermentation process is predicted with the aid of the process model. If a difference between the value predicted with the process model and a target value for concentration of the at least one substrate of the fermentation process is greater than a predetermined threshold value, a control system will intervene in the fermentation process and at least one operating parameter of the fermentation process will be adjusted.

In such cases, it is however not taken into account that bioprocesses will vary when repeated even if the conditions are the same and can thus deliver high quality products even if they deviate from the corresponding process model. An adjustment of the ongoing bioprocess to the process model by an intervention may therefore not be necessary with each detected variance. There may be different reasons for a detected variance, such as errors in the process (e.g., failure of regulatory mechanisms or sensors in the bioreactor, contaminations, or incorrect gassing) biological variability (e.g. differences in the preparatory culture of the biomass used or differences in the cell strain) or variability in the process control (e.g., differences in the raw materials, fluctuations in the substrate composition, or differences in the technical equipment). Depending on the cause of the detected variance, intervention in the bioprocess, such as in the event of process errors, may be necessary to prevent damage to equipment, for instance, or in the worst case to discontinue the bioprocess. Detected variances, which arise, for instance, on account of biological variability or variability of the process control, are in most cases not harmful to the product quality and therefore require no intervention. Typically, based on the process model, it is not possible to infer the different cause of the respective detected variance between model-based prediction and the process as it is actually running, because the variances cannot be evaluated. The detected variance therefore does not indicate whether the variance is only a biological variability or a variability of the process control or whether it is a serious process error. As a result, the quality of the prediction via the process model is unclear on the one hand, and on the other hand in the case of doubt it may possibly result in unnecessary interventions and/or discontinuations of bioprocesses, as well as additional costs.

SUMMARY OF THE INVENTION

In view of the foregoing, it is an object of the invention to therefore provide a method for monitoring bioprocesses, in which a prediction quality of a process model employed to predict a bioprocess can be easily evaluated and increased and detected variances between the process model and the course of the bioprocess can be evaluated accordingly in terms of quality.

This and other objects and advantages are achieved in accordance with the invention by a method comprising:
  a. selecting at least one process parameter of a bioprocess, for which current measured values are determined during the course of the bioprocess;
  b. comparing the respective current measured value of the at least one selected process parameter with the corresponding estimated value estimated by the process model for this at least one process parameter;
  c. comparing a variance between the respective current measured value and the corresponding estimated value for the at least one selected process parameter with a predetermined threshold value; and
  d. modifying at least one defined model parameter employed in the process model when the predetermined threshold value is exceeded on account of the variance between the respective current measured value and the corresponding estimated value for the at least one selected process parameter.

In such cases, steps b) to d) of the method with the model parameter in each case modified in step d) are executed through until the variance between the respective measured value and the corresponding estimated value for the at least one selected process parameter is placed below the threshold value. The method is discontinued and a corresponding warning output to the operator if, for instance, after a predetermined number of repetitions of steps b) to d), the threshold value of the variance between the respective measured value and the corresponding estimated value is met for the at least one selected process parameter.

The main concept of the inventively proposed solution consists in it being possible to easily and quickly adjust the process model to the actual course of the process by varying a defined model parameter of the process model in the case of variances between the current course of the process and the prediction based on the process model. Improved estimated values for the selected process parameters, but also for the further process parameters, which are estimated with the process model, can thus be obtained. The quality of the prediction of the bioprocess by the process model can thus be easily increased to a high-quality level.

Furthermore, developing variances can be classified very quickly and easily in terms of quality using the iterative, inventive method. A distinction can easily be made, for instance, between biological variability or variability in the process control (e.g., differences in the preparatory culture or in the cell strain used, differences in the raw material or substrate for the bioprocess) and errors in the bioprocess itself (e.g., incorrect gassing, or incorrect regulation of the pH value). If a variance is evaluated as an error in the bioprocess, then an operator can rapidly intervene to prevent damage to equipment, for instance, or if necessary a discontinuation of the bioprocess. The reason for which the variance in the process occurs and whether an intervention in the course of the bioprocess is required can be easily inferred with the inventive method. Unnecessary interventions in the bioprocess or unnecessary discontinuations can thus be prevented or at least reduced via the method in accordance with the invention.

In a further embodiment of the invention, it is advantageous if what is known as a lag term is used as a defined model parameter, which is employed in the process model. If the threshold value is exceeded on account of the variance between the respective measured value and the corresponding estimated value for the at least one selected process parameter, then the lag term is modified within predetermined limit values. The limit values, within which the lag term is varied, are ideally predetermined by a biomass used in the bioprocess, in particular by the bioactive cells or organisms employed therein. Depending on the biomass employed in each case, e.g., cell strain or preparatory culture employed for the biomass used, a bioprocess can run slightly faster or slower. In the process model, this is taken into account by what is known as the "lag term". In step d), the process model can be very easily modified or adjusted to a possible biological or process-specific variability by varying the lag term within biologically meaningful limit values.

With a predetermined number of repetitions of steps b) to d), the variance between the measured value and the estimated value cannot be eliminated for the at least one selected process parameter, i.e., the threshold value is further exceeded in spite of the variation in the lag term, so the variance can be evaluated in the process as a process variance or as an error. At least one warning can then be sent to the operator, for instance, such as to examine the process, or to monitor the sensor technology. Furthermore, it is possible to derive herefrom that the estimated values are not valid for the further process parameters and for variables that cannot be measured directly, known as soft sensors.

If the variance between the measured value and the estimated value can be rectified for the at least one selected process parameter by the variation in the lag term within the predetermined number of repetitions of steps b) to d), then the variance can be classified as a biological variability determined, for instance, by a difference in the preparatory culture or cell culture employed or in the cell strain employed, for instance. The bioprocess can thus proceed further. The further process parameters predicted with the process model can be classified as valid.

It is favorable if a process parameter of the bioprocess, for which during the course of the bioprocess measured values can be determined approximately in real time, is selected as the process parameter to be measured. For this reason, the variance between the process model and the course of the bioprocess can be determined approximately in real time, particularly if the process model is calculated in parallel with the ongoing bioprocess. A direct comparison between the measured value of the selected process parameter and the estimated value calculated or predicted by the process model can thus be performed for the process parameter. A near-instant intervention is thus also enabled if there is an error in the bioprocess.

Expediently the repetitions of steps b) to d) of the inventive method, i.e., comparison between measured value and estimated value of the selected process parameter. Here, comparisons of the variance with the predetermined threshold value and modification of the model parameter of the process model when the threshold value is exceeded, are performed with the respective modified model parameter at short intervals in time such as every 10 seconds. The process model can thus be rapidly adjusted, e.g., with the presence of biological variability or variability in the process control (e.g., differences in the raw materials, or fluctuations in the composition of the substrate) so that a correspondingly valid prediction of the bioprocess can be performed for the further course of the process. In case of errors in the bioprocess, a near-instant response can occur. A near-instant intervention allows damage to the bioprocess and/or to the equipment, for instance, to be avoided or prevented.

In a preferred embodiment of the invention, what is known as the respiratory quotient, also abbreviated to RQ, is selected as a process parameter that is measured during the course of the bioprocess. The respiratory quotient is a process parameter in bioprocesses, in particular in fermentation processes, which represents an indicator of the processes within a bioactive cell. The respiratory quotient describes a ratio of the carbon dioxide quantity ($CO_2$) produced at a given time to the oxygen ($O_2$) consumed at the same time. During the course of a bioprocess, the respiratory quotient can be measured very easily in real time, e.g., using what is known as off-gas analysis.

As an alternative or additionally, a concentration of the biomass and/or a concentration of the substrate can be selected as process parameters, which are measured during the course of the bioprocess. The determination of the current measured values of the concentration of the biomass during the course of the bioprocess occurs, for instance, based on the electrical properties of the biomass. Current measured values for the concentration of the substrate (e.g., glucose etc.) can likewise be determined in the course of the bioprocess, such as based on spectroscopic properties using spectroscopy, in particular using reflection spectroscopy.

Furthermore, it is advantageous if what is known as a deterministic process model is employed to estimate the process parameters of the bioprocess. With a deterministic approach for an illustration of a bioprocess as a model, the knowledge of the respective process-specific, biochemical processes inside and outside of the biomass or cells employed is converted into mathematical equations during the course of the bioprocess.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will now be described by way of example, making reference to the accompanying drawing, in which:

The FIGURE shows a schematic representation of an exemplary course of the inventive method for monitoring bioprocesses, the course of which is predicted with the aid of a process model.

DETAILED DESCRIPTION OF THE EXEMPLARY EMBODIMENTS

The FIGURE shows a schematic representation of an exemplary course of the inventive method for monitoring bioprocesses based on an exemplary bio or fermentation process with baker's yeast or *S. cerevisiae* as biomass X. Other bioactive organisms (fungi, bacteria), such as *E. coli*, or mold, can however also be employed as biomass X in bioprocesses. The bio or fermentation process typically occurs in a bioreactor, in which the environmental and reaction conditions can be optimized and controlled for a bioprocess, such as a fermentation with baker's yeast. To this end, during the bioprocess various environmental and/or process parameters X, S, E, pO2, RQ are regulated and/or measured in the bioreactor such as pH value, temperature, oxygen supply, nitrogen supply, mixer settings, glucose concentration S, concentration of the biomass X or of the substance E to be produced (e.g. ethanol), concentration of dissolved oxygen pO2 or what is known as the respiratory quotient RQ.

Monitoring of the bioprocess is necessary to maintain and regulate the environmental and reaction conditions. To this end, a process model PM is produced for the course of the bioprocess, with which process model estimated values $X_c$, $S_c$, $E_c$, $pO2_c$, $RQ_c$ for the respective biological process parameters X, S, E, pO2, RQ, which are relevant to a monitoring and regulation, for instance, can be estimated or calculated for each time segment during the course of the bioprocess. With a fermentation process with baker's yeast, a concentration of biomass C, glucose S, ethanol E, dissolved oxygen pO2 and what are known as respiratory quotients RQ can be determined for the monitoring with the process model PM on the basis of initial values $X_0$, $S_0$, $E_0$, $pO2_0$. Depending on the respective bioprocess, further and/or other process parameters can also be estimated with the aid of the respective process model PM. Corresponding initial values of the process parameters X, S, E, pO2 of the real bioprocess are typically used as initial values $X_0$, $S_0$, $E_0$, $pO2_0$ of the process parameters X, S, E, pO2 for the process model PM.

A deterministic process model PM can be used to estimate the process parameters X, S, E, pO2, RQ for the respective time segment of the bioprocess, for instance, of which deterministic process model PM the knowledge of the respective process-specific, biochemical processes inside and outside of the employed biomass or cells is translated into mathematical equations during the course of the bioprocess. Furthermore, the process model PM can contain at least one defined model parameter $\alpha$ with an initial value $\alpha_0$. This model parameter $\alpha$ may be what is known as a lag term $\alpha$, for instance, which is used to take into account that the bioprocess or the fermentation can occur more quickly or slowly using baker's yeast depending on the operator, cell strain of the biomass C, preparatory culture of the biomass X, on account of fluctuations in the substrate S, etc., in particular in spite of otherwise identical conditions.

The method in accordance with the invention begins with a start step, with which the bioprocess or the fermentation with baker's yeast is started in the bioreactor by adding the biomass X to the substrate or glucose S, for instance. The calculation or estimation of the process parameters X, S, E, pO2, RQ for each time segment of the bioprocess is started in parallel with the starting step based on the initial values $X_0$, $S_0$, $E_0$, $pO2_0$ of the process parameters X, S, E, pO2 by the process model PM. Bioprocess or fermentation and process model are largely to proceed in parallel. At the starting step, the initial value $\alpha_0$ of the model parameter $\alpha$ or lag term $\alpha$ is employed in the process model PM and the process parameters X, S, E, pO2, RQ are estimated accordingly.

In a first method step a), at least one process parameter X, S, E, pO2, RQ of the bioprocess is selected. During the course of the bioprocess current measured values $RQ_m$ are determined for this selected process parameter RQ. Ideally the measured values $RQ_m$ of the selected process parameter RQ can be determined approximately in real time during the course of the bioprocess. In the present exemplary course of the method for a fermentation with baker's yeast, what is known as the respiratory quotient RQ was selected as the process parameter $RQ_m$ to be measured, for instance. The respiratory quotient RQ describes a ratio of the carbon dioxide quantity ($CO_2$) produced at a given time to the simultaneously consumed oxygen ($O_2$) and represents an indicator of processes within a bioactive cell. During the bioprocess or during the fermentation the process parameter RQ can be measured relatively easily in real time, such as using what is known as off-gas analysis.

Alternatively or in addition, in the first method step, a concentration of the biomass X and/or a concentration of the glucose S can also be selected with the exemplary bioprocess (fermentation with baker's yeast), as the process parameter $X_m$, $S_m$ to be measured. The respective concentration of the biomass X can be measured during the course of the fermentation on the basis of the electrical properties of the cells or the biomass X, for instance. The respective concentration of the glucose S can be currently determined, e.g., with the aid of spectroscopy, in particular reflection spectroscopy, based on spectroscopic properties of the substrate during the course of the fermentation.

In a second method step b), a current measured value $RQ_m$ of the selected process parameter RQ is then compared with the corresponding estimated value $RQ_c$ of the selected process parameter RQ estimated by the process model PM. This can be performed approximately in real time when the bioprocess and process model are run in parallel. That is, a current measured value $RQ_m$ for the respiratory quotient RQ and an estimated value $RQ_c$ determined for the measuring time instant by the process model PM are determined as synchronously as possible for the respiratory quotient RQ during the course of the fermentation and then compared with one another. The comparison can be realized as subtracting the estimated value $RQ_c$ from the measured value $RQ_m$ or as subtracting the measured value $RQ_m$ from the estimated value $RQ_c$. If the measured value $RQ_m$ and the estimated value $RQ_c$ for the respective time instant are not identical, then a variance $\Delta RQ$ is provided by the subtraction.

In a third method step c), the variance $\Delta RQ$ between the respective current measured value $RQ_m$ and the corresponding estimated value $RQ_c$ is compared with a predetermined threshold value. On account of the comparison via subtraction the variance $\Delta RQ$ between measured value $RQ_m$ and estimated value $RQ_c$ can have a positive or negative sign. As a result, a sum of the variance $\Delta RQ$ determined in the second method step b) is used for the comparison with the predetermined threshold value.

If it is established in the third method step c) that the variance $\Delta RQ$ or the sum of the variance $\Delta RQ$ is less than the predetermined threshold value, then the process model PM is classified as a good prediction of the course of the bioprocess or fermentation. That is, it is assumed therefrom that valid estimated values $X_c$, $S_c$, $E_c$, $pO2_c$ of the further process parameters X, S, E, pO2 are provided by the process model PM and in the course of the bioprocess or fermentation these estimated values $X_c$, $S_c$, $E_c$, $pO2_c$ can be used for a monitoring. The inventive method is ended with the validation of the used process model PM.

If it is established in the third method step c) that the variance $\Delta RQ$ or the sum of the variance $\Delta RQ$ has exceeded the predetermined threshold value, then a fourth method step d) is performed. In the fourth method step d), the defined model parameter $\alpha$ employed in the process model PM, such as the lag term $\alpha$, changes within predetermined limit values. The limit values for this change in the model parameter $\alpha$ are predetermined, for instance, by the biomass X used in the bioprocess. In the present example, a lag term $\alpha$ is employed as the model parameter $\alpha$ for the inventive method and baker's yeast or the bioactive organism S. cerevisiae is used as biomass X for the bioprocess or fermentation. This thus also specifies the limit values for the variation of the model parameter $\alpha$ or lag term $\alpha$. This means that in the fourth method step d), the model parameter $\alpha$ or the lag term $\alpha$ of the process model PM is changed from an initial value $\alpha_0$ to a new value $\alpha_1$, where the new value $\alpha_1$ for the lag term has to lie within the predetermined limit values.

Subsequently the second and the third method step b), c) are run through again, where the new estimated value $RQ_c$ of the selected process parameter RQ is calculated for the now current time segment by the bioprocess of the process model PM with the changed value $\alpha_1$ of the model parameter $\alpha$ or lag term $\alpha$. This new estimated value $RQ_c$ is then compared with a now current measured value $RQ_m$ of the selected process parameter RQ in the repetition of the second method step b). In the repetition of the third method step c), the variance $\Delta RQ$ that is determined based on the now current values for the measured value $RQ_m$ and the estimated value $RQ_c$ or the sum of this variance $\Delta RQ$ is compared again with the predetermined threshold value. If the variance $\Delta RQ$ or the sum of the variance $\Delta RQ$ is now less than the predetermined threshold value, then the original variance $\Delta RQ$ that is above the threshold value and, which has been established during a first or preceding run of the second and third method step b), c), is assessed as a biological variability or as a variability in the process control for instance. The bioprocess or the fermentation can thus be continued and the predictions $X_c$, $S_c$, $E_c$, $pO2_c$ of the further process parameters X, S, E, pO2 can thus be classified as "validated". The method is then terminated.

If in the repetition of the third method step c) the threshold value is again exceeded by the newly determined variance $\Delta RQ$, then the fourth method step d) can be performed again. That is, the model parameter $\alpha$ or the lag term $\alpha$ can be again varied within the predetermined limit values. The second to fourth method steps b), c), d) can then be run through with a respective modified model parameter $\alpha$ or lag term $\alpha$ for the process model PM until the respective determined variance $\Delta RQ$ is placed below the predetermined threshold value. With this variance $\Delta RQ$, the predictions of the further process parameters X, S, E, pO2 can then be considered as validated and the method can be terminated. The established variances $\Delta RQ$ can be classified again as biological variability or variability which barely influence the bioprocess.

Ideally the respective repetitions of the second to fourth method steps b), c), d) are performed with the respective modified model parameter α or delay term α for the process model PM in short intervals in time (e.g., 10 seconds), in order quickly to arrive at a validated process model PM or at a high-quality classification of the detected variances ΔRQ.

In the case that after a predetermined number of repetitions of the second to fourth method step b), c), d) with a respective changed model parameter α or lag term α for the process model PM, the predetermined threshold value of the respective detected variance ΔRQ between the respective current measured value $RQ_m$ and the corresponding estimated value $RQ_c$ of the selected process parameter RQ is still exceeded, the method is discontinued. A warning to the operator can then be output, for instance, in order to effect an intervention in the bioprocess or the fermentation. With this intervention, the bioprocess can be assessed and, e.g., the sensor technology monitored. In the worst case the bioprocess must be terminated.

In the case that the variance ΔRQ cannot be eliminated by repeatedly varying the model parameter α, this variance ΔRQ is considered to be a "process variance" or it is assumed herefrom that there is an error in the process, such as a failure of the pH value control, a faulty or incorrect gassing, or contamination in the reactor. The estimated values $X_c$, $S_c$, $E_c$, $pO2_c$ of the further process parameters X, S, E, pO2 which are determined with the process model PM can thus be classified as "not validated". By repeating the second to fourth method step b), c), d), with the respective modified model parameter α or lag term α for the process model PM at short intervals in time (e.g. 10 seconds), in this case a near-instant and quick reaction can be made. Possible damage to the bioprocess and/or equipment can thus be avoided.

On the whole the inventive method is advantageous in that a number of bioprocesses, which in case of doubt are otherwise discontinued, is reduced, so that a developing variance ΔRQ between the respective current measured value $RQ_m$ and the corresponding estimated value $RQ_c$ of the selected process parameter RQ can be evaluated and classified in terms of quality. As a result, the efficiency in the use of resources and raw materials can be increased and the operating costs can be minimized.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for monitoring bioprocesses, a course of a bioprocess in a bioreactor being predicted aided by a process model and estimated values for biological process parameters being estimated during the course of the bioprocess with the process model, the method comprising:
   a) selecting at least a respiratory quotient as at least one process parameter of the bioprocess, for which measured values are determined during the course of the bioprocess in the bioreactor;
   b) comparing a respective measured value of the at least one selected process parameter with a corresponding estimated value of the at least one process parameter estimated by the process model;
   c) comparing a variance between the respective measured value and the corresponding estimated value of the at least one selected process parameter with a predetermined threshold value; and
   d) changing at least a lag term employed as a defined model parameter in the process model when the predetermined threshold value is exceeded by the variance to adjust the process model to an actual course of the bioprocess in the bioreactor;
   wherein the steps b) to d) with a respective changed model parameter are repeated until the variance is placed below the predetermined threshold value;
   wherein the lag term, which is employed as the defined model parameter in the process model, is changed within predetermined limit values when the predetermined threshold value is exceeded by the variance during said step d); and
   wherein in cases that, after a predetermined number of repetitions of steps b) to d), the predetermined threshold value is still exceeded by the variance, the bioprocess in the bioreactor is discontinued to prevent damage to the bioreactor and a warning is output.

2. The method as claimed in claim 1, wherein limit values for changing the lag term are predetermined by a biomass employed in the respective bioprocess.

3. The method as claimed in claim 2, wherein the biomass comprises one of bioactive cells and organisms.

4. The method as claimed in claim 1, wherein a process parameter of the bioprocess is selected as a process parameter to be measured, for which during the course of the bioprocess measured values are determinable approximately in real time.

5. The method as claimed in claim 1, wherein the respective repetitions of steps b) to d) are performed with the respective changed model parameter at short intervals of time in relation to one another.

6. The method as claimed in claim 1, wherein at least one of (i) a concentration of the biomass and (ii) a substrate is further selected as the at least one process parameter which is measured during the course of the bioprocess.

7. The method as claimed in one of the preceding claim 1, wherein a deterministic process model is employed to estimate the biological process parameters of the bioprocess.

8. The method as claimed in claim 1, wherein the bioprocesses comprise fermentation processes.

* * * * *